US010156507B2

(12) United States Patent
Davidson et al.

(10) Patent No.: US 10,156,507 B2
(45) Date of Patent: Dec. 18, 2018

(54) DETERMINATION OF FREE VOLUME OF A ROCK SAMPLE USING HIGH PRESSURE ADSORPTION DATA

(71) Applicant: Schlumberger Technology Corporation, Sugar Land, TX (US)

(72) Inventors: Benjamin Howard Davidson, West Jordan, UT (US); Keith Howarth Greaves, Salt Lake City, UT (US); David Clark Atwood, North Salt Lake, UT (US); Robert Michael Griffin, Salt Lake City, UT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 401 days.

(21) Appl. No.: 14/676,210

(22) Filed: Apr. 1, 2015

(65) Prior Publication Data

US 2016/0290907 A1    Oct. 6, 2016

(51) Int. Cl.
*G01N 31/00*    (2006.01)
*G01N 7/04*    (2006.01)
(Continued)

(52) U.S. Cl.
CPC ........... *G01N 7/04* (2013.01); *G01N 15/0893* (2013.01); *G01N 33/24* (2013.01)

(58) Field of Classification Search
CPC .................................. G01N 7/04; G01N 33/24
(Continued)

(56) References Cited

U.S. PATENT DOCUMENTS 5,239,482 A * 8/1993 Ajot ................... G01N 15/0893
702/30
5,342,580 A * 8/1994 Brenner ................... G01N 7/04
422/88

(Continued)

FOREIGN PATENT DOCUMENTS

WO    WO2014123973 A1    8/2014
WO    WO2015034463 A1    3/2015

OTHER PUBLICATIONS

SPE20728 M.J. Mayor et al.; Measurement and Evaluation of Coal Sorption Isotherm Data; pp. 157-170.

(Continued)

*Primary Examiner* — Jay C Kim

(57) ABSTRACT

A method of characterizing free volume of a rock sample includes test operations that measure pressure decay data from stepwise pressurization of the rock sample with a test gas. An initial free volume of the rock sample is calculated as a function of the pressure decay data. An initial maximum storage capacity of the rock sample is derived as a function of the initial free volume of the rock sample. A volume of test gas adsorbed as a liquid is calculated based on the maximum storage capacity of the rock sample. An updated free volume of the rock sample is calculated based on the initial free volume and the volume of the test gas adsorbed as a liquid. An updated maximum storage capacity of the rock sample is derived as a function of the updated free volume. Calculations of the volume of test gas adsorbed as a liquid, the updated free volume and the updated maximum capacity of the rock sample can be repeated until the updated maximum storage capacity and the updated free volume converge respectively to give the maximum storage capacity and free volume of the rock sample.

11 Claims, 5 Drawing Sheets

(51) Int. Cl.
*G01N 33/24* (2006.01)
*G01N 15/08* (2006.01)

(58) Field of Classification Search
USPC .......................................................... 702/30
See application file for complete search history.

(56) References Cited

U.S. PATENT DOCUMENTS

| | | | |
|---|---|---|---|
| 8,881,587 B2* | 11/2014 | Valenza, II | G01N 15/082 |
| | | | 73/152.07 |
| 9,709,478 B2* | 7/2017 | Chertov | G01N 15/088 |
| 2012/0223235 A1 | 9/2012 | Maucec | |
| 2014/0352984 A1 | 12/2014 | Enis et al. | |
| 2014/0366621 A1 | 12/2014 | Valenza et al. | |
| 2015/0219782 A1* | 8/2015 | Kadayam Viswanathan | ............... |
| | | | G01V 3/32 |
| | | | 324/309 |

OTHER PUBLICATIONS

Daniel JK Ross et al.; Impact of Mass Balance calculations on adsorption capacities in microporous shale gas reservoirs: pp. 1-11.
International Search Report and Written Opinion issued in the related PCT Application PCT/US2015/063215, dated Feb. 22, 2016 (10 pages).
International Preliminary Report on Patentability issued in the related PCT Application PCT/US2015/063215, dated Oct. 3, 2017 (5 pages).

* cited by examiner

DETERMINATION OF FREE VOLUME OF A ROCK SAMPLE USING HIGH PRESSURE ADSORPTION DATA

BACKGROUND

Field

The present application relates to the determination of free volume in a rock sample.

Description of Related Art

In shale or coal, gas is adsorbed on the surface of the kerogen. This gas is referred to as "adsorbed gas." Gas is also freely distributed in the pore space of the shale. This is referred to as "free gas." The total gas in place (GIP) is the combination of adsorbed gas and free gas. Depending on the initial pressure of the reservoir, as free gas is produced and the pore pressure falls, adsorbed gas will be liberated, or desorb, from the surface of the kerogen.

Scientists sometimes use canister desorption tests to determine the total GIP from cores. Immediately upon retrieval, freshly cut core samples are sealed in canisters and sent to the laboratory for testing. The gas is removed from the canister, volumetrically measured and compositionally analyzed as a function of time. A plot of gas produced over time can be used to estimate the GIP for the core sample at reservoir conditions. This analysis is sensitive to the amount of time it takes to retrieve the core from downhole.

To determine adsorbed gas volume for shales engineers use pressure relationships that estimate the sorptive potential of the rock. Samples are pulverized to maximize surface area and then heated to drive off any adsorbed gas. Alternatively, the samples may be saturated with water or used in "as received" condition. Samples are then exposed to methane at increasingly high pressure while held at a constant temperature (i.e., isothermally). A sorption isotherm is a laboratory measurement performed on a representative sample to determine the gas storage capacity as a function of pressure. The term "isotherm" is used because the experiment is conducted at constant temperature, which is generally set to be equal to the temperature of the reservoir.

The volume of gas adsorbed by the rock sample, presented in units of standard cubic feet/ton (scf/ton), is described by a Langmuir isotherm curve such as that shown in FIG. 1. The Langmuir isotherm (labeled gas content in FIG. 1) is derived from crushed rock samples and quantifies a rock's adsorbed storage capacity. The Langmuir volume, $V_L$, is the theoretical limit for gas adsorption at infinite pressure. Storage capacity at a given pressure, p, can be determined from the Langmuir isotherm. The Langmuir pressure, $P_L$, is defined as the pressure at half the Langmuir volume.

As shown in FIG. 2, using the Langmuir isotherm, the total GIP for a specific reservoir can be determined as a function of pressure. The total gas is the gas adsorbed to kerogen plus free gas stored in pores. At low pressures, adsorption is an effective gas storage mechanism. As the pressure increases, pore gas correspondingly increases. Productivity of most of the organic shale reservoirs being developed today is driven by the volume of pore gas. Desorption becomes important as the bottomhole flowing pressure declines.

Once an isotherm is established, the storage capacity of the rock can be determined by referencing the pore pressure of the formation, which is representative of the in situ reservoir pressure. More and more isotherm tests are being performed on low adsorption shales. Although samples with total organic carbon (TOC) content of less than 2.5% are not typically run, running of low TOC content samples is becoming more common by some isotherm labs. However, existing isotherm testing on such low adsorption shales may generate isotherm data that indicates a negative slope at higher pressures instead of flattening out as shown in FIG. 1.

SUMMARY

In a first aspect, a new data reduction technique is provided to address the issues noted above related to isotherm data quality for low-porosity, low-adsorption shales. This technique attempts to handle issues of shale pore size by pressurizing the sample using a test gas other than helium, at pressures above the pressure when the maximum storage capacity is reached, to determine the free volume. The described technique may reduce errors caused by void volumes being available to helium molecules (when conventionally tested with helium), but not available to the larger test gas molecules, such as methane or nitrogen.

According to one aspect, a method of characterizing free volume of a rock sample includes test operations that measure pressure decay data from stepwise pressurization of the rock sample with a test gas. An initial free volume of the rock sample is calculated as a function of the pressure decay data. A maximum storage capacity of the rock sample is derived as a function of the initial free volume of the rock sample. A volume of test gas adsorbed as a liquid is calculated based on maximum storage capacity of the rock sample. An updated free volume of the rock sample is calculated based on the initial free volume and the volume of the test gas adsorbed as a liquid. An updated maximum storage capacity of the rock sample is derived as a function of the updated free volume. The calculations of the volume of test gas adsorbed as a liquid, the updated free volume, and the updated maximum capacity of the rock sample can be repeated until the updated maximum storage capacity and the updated free volume converge, respectively, to give the maximum storage capacity and free volume of the rock sample.

DETAILED DESCRIPTION

It has been proposed that using helium to determine the sample free volume may produce an error if the effects of pore size-dependent void volume (porosity) are not considered. See, Daniel J. K. Ross and R. Marc Bustin, "Impact of Mass Balance Calculations on Adsorption Capacities in Microporous Shale Gas Reservoirs", *Fuel*, Volume 86, Issues 17-18, December 2007, pp. 2696-2706, http://dx.

doi.org/10.1016/j.fuel.2007.02.036 (http://www.sciencedirect.com/science/article/pii/S0016236107001202).

More particularly, Ross et al. propose that the error in adsorption calculations due to helium void volume calibrations for high pressure methane isotherms is most significant with low organic carbon content, moisture equilibrated shales, and mudrocks in which the overall adsorptive capacity is low. In such samples negative adsorption can be calculated due to the void volume of helium used in the mass balance calculations exceeding the void volume of methane—a reflection of greater pore space accessibility of the smaller helium molecule than the larger methane molecule. In order to address the issue of the pore space being available to helium, a workflow is described for determining the free volume in a shale sample by using a test gas other than helium, such as methane.

Figure 1:
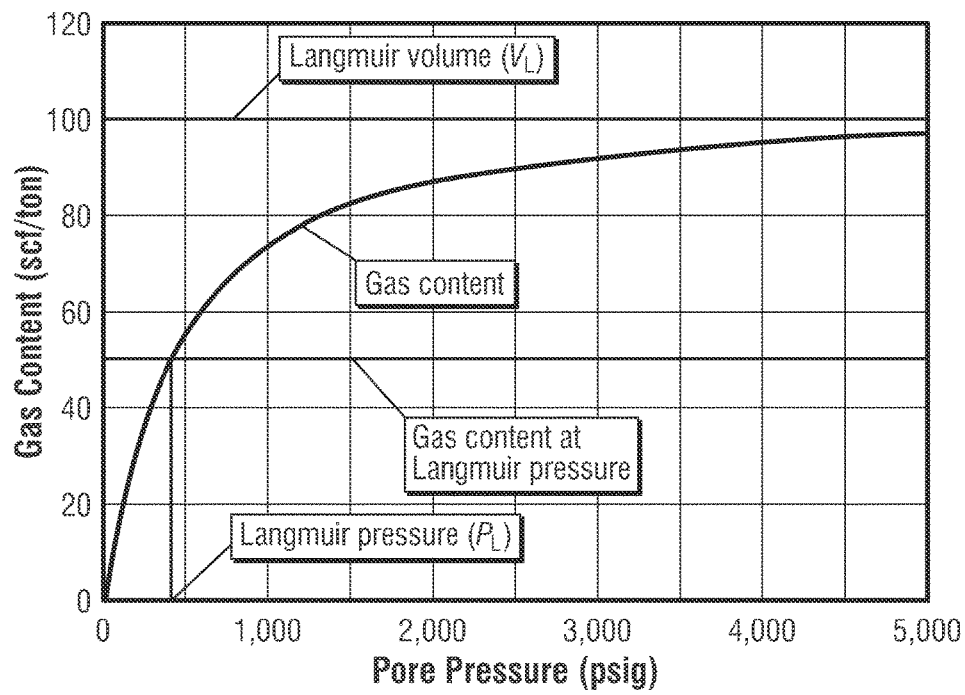
FIG. 1 is an example of a Langmuir curve.
Figure 2:
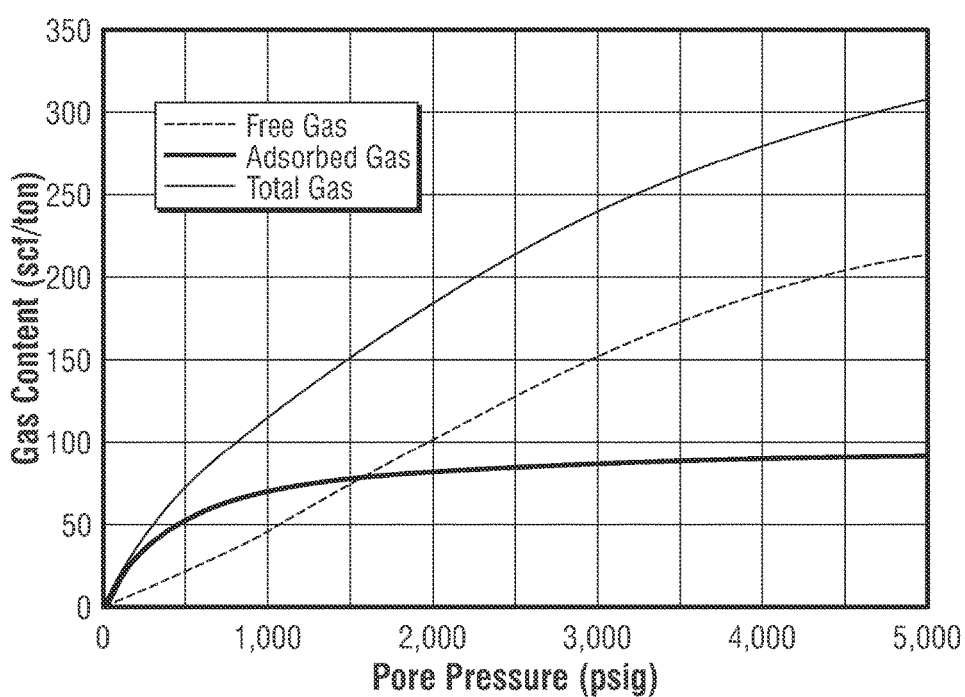
FIG. 2 is a graph showing gas content as a function of pressure.

As will be appreciated by those of skill in the art, the term "free volume" refers to the total pore space in a sample that can hold the un-adsorbed gas. When gas is adsorbed, it is stored on the surface of the sample in liquid form, which occupies a volume in the pore space that subtracts from the free volume. Typical isotherm tests show that the storage capacity of a sample (which represents the amount of test gas adsorbed by the sample) approaches a maximum value (i.e., the Langmuir volume, FIG. 2) when the pressure of the surrounding gas is at least a certain pressure (i.e., 4000 psig in FIG. 2).

Figure 3:
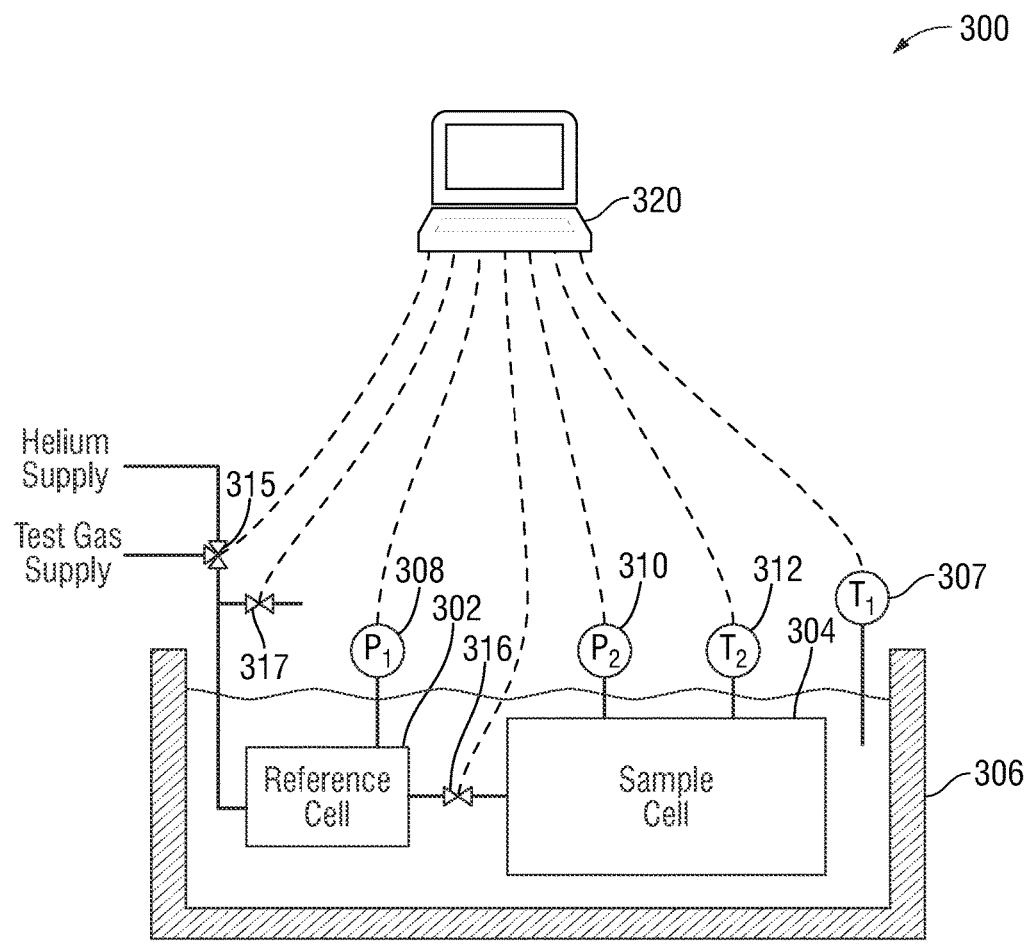
FIG. 3 is a schematic diagram of a test apparatus that may be used with an embodiment of a workflow.

FIG. 3 shows a schematic of a modified Boyle's Law porosimeter 300 that may be used according to a workflow described below for determining a storage capacity and a free volume of a shale sample. The porosimeter 300 includes a reference cell 302 and a sample cell 304. All cell and tubing volumes can be known accurately. The reference and sample cells 302, 304 are immersed in a water or oil bath or heated air chamber 306 that is temperature controlled to maintain the temperature substantially constant (e.g., within +/−0.25° F. of a set temperature). The bath temperature is monitored by a temperature sensor 307 and may be set to approximate the temperature of the well from which the sample was extracted. Pressures in the reference and sample cells 302, 304 are respectively monitored with pressure sensors 308, 310. The internal temperature of the sample cell 304 may be monitored with a temperature sensor 312 to ensure stability during the experiment.

The reference cell 302 is fluidly coupled to a helium supply and to a test gas supply by a three-way valve 315, which may be electrically controlled. A vent valve 317, which may be electrically controlled, is positioned in the helium/test gas supply line. The reference cell 302 and the sample cell 304 are fluidly coupled by a valve 316, which likewise may be electrically controlled.

The porosimeter 300 also includes a controller and/or computer processing system 320 that includes control logic that interfaces to the electrically controlled valves 315, 316 via wired or wireless signal paths therebetween for control of the operation of the valves 315, 316, that interfaces to the pressure sensors 308, 310 via wired or wireless signal paths therebetween for pressure measurements and recordation of such pressure measurements during operation of the porosimeter 300, and that interfaces to the temperature sensors 307, 312 via wired or wireless signal paths therebetween for temperature measurements and recordation of such temperature measurements during operation of the porosimeter 300. The control logic of the controller and/or computer processing system 320 (which can be embodied in software that is loaded from persistent memory and executed in the computing platform of the computer processing system 320) is configured to control the different parts of the porosimeter 300 to carry out a sequence of operations (workflow) that characterizes the free volume of the sample placed in the sample cell 304. The control logic can be configured by user input or a testing script or other suitable data structure, which is used to configure the controller or the computer processing system 320 in order to carry out control operations that are part of the workflow as described herein. For example, the user input or the testing script or other suitable data structure can specify parameters (such as pressures, flow rates, temperatures, etc.) for such control operations of the workflow.

Figure 4:
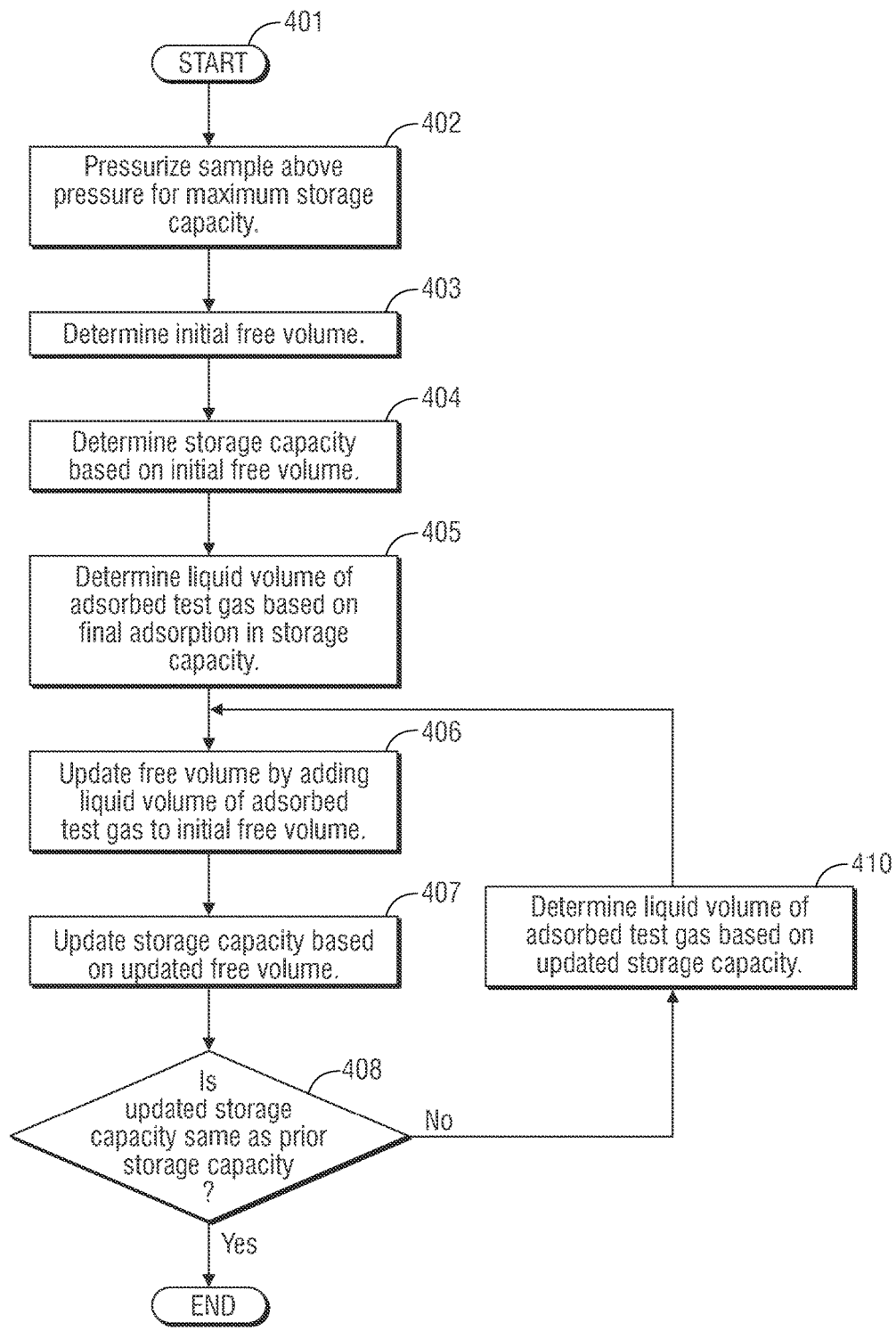
FIG. 4 illustrates an embodiment of a workflow.

An embodiment of a workflow is illustrated in the flow chart of FIG. 4. As a preliminary matter before the start of the workflow, a sample is prepared, the volumes of the reference cell 302 and the sample cell 304 are measured, and the sample is introduced into the sample cell 304. The sample may be prepared by pulverizing the sample to maximize its surface area and then by heating the pulverized sample to drive off any adsorbed gas or it may be saturated with water or used in "as received" condition. The helium supply connected to the porosimeter 300 may be used to determine the volumes of the reference and sample cells 302, 304. For example, the volumes of the reference and sample cells 302, 304 are determined, such as by Boyle's law helium expansion, after placing a sphere of known volume in the sample cell, as is known in the art. Thus, at block 401 the sample is positioned in the sample cell 304 and is ready to be incrementally pressurized with a test gas (e.g., methane) as follows.

At block 402 the sample is pressurized in stages to a pressure above the pressure at which adsorption of the test gas does not predominate. This pressure can be defined as the pressure corresponding to a certain percentage of the Langmuir volume. For example, a pressure above the pressure corresponding to 85% of the Langmuir volume could be used as a pressure threshold. Also, the pressure can be a pressure above the pressure which the sample is subject to in the rock formation. For example, the valve 316 is initially closed to isolate the sample cell 304 from the reference cell 302. The valve 315 is positioned to introduce test gas into the reference cell 302 to pressurize the reference cell 302 to an initial pressure of about 100 psig (7.03 kg/square cm gauge) for the first stage. With the reference cell 302 charged to a known pressure, the initial pressures $P_1$ and $P_2$ of the reference and sample cells 302, 304 are recorded and the valve 315 is then closed. With the valve 315 closed and the reference cell 302 charged, the valve 316 is opened to allow the test gas from the reference cell 302 to move into the sample cell 304 where some of the test gas can adsorb into the sample. After a time period elapses, the pressures $P_1$ and $P_2$ in the sample cell 304 and reference cell 302 will equilibrate. During this time period the pressures $P_1$ and $P_2$ are recorded. Once the pressures are equilibrated, the final pressures $P_1$ and $P_2$ are recorded and valve 316 is closed. Then, these operations are repeated for further stages of pressurization. The process of charging and equalizing pressure may be repeated multiple times, such as nine times, each time increasing the final pressures of $P_1$ and $P_2$ until the final pressure of $P_2$ corresponds to the pressure threshold mentioned above.

Pressure test data for nine pressurization stages or data runs is shown below as a matrix. As indicated, at the end of the pressurization the test sample is pressurized to 3857 psig (271.1 kg/square cm gauge). Also, for each test run, compressibility factors (z) are determined (as will be appreciated by those of skill in the art), as shown in the matrix

| REFERENCE CELL | | SAMPLE CELL | |
|---|---|---|---|
| Initial *psig* | Final *psig* | Initial *psig* | Final *psig* |

$$Press := \begin{pmatrix} 103.37 & 47.50 & 0.02 & 47.79 \\ 148.75 & 95.19 & 48.33 & 95.74 \\ 298.51 & 191.86 & 96.07 & 192.43 \\ 607.14 & 391.15 & 192.82 & 391.69 \\ 1195.18 & 780.18 & 392.11 & 781.11 \\ 1995.86 & 1368.04 & 781.74 & 1368.68 \\ 3000.39 & 2144.01 & 1369.28 & 2144.32 \\ 3809.96 & 2922.05 & 2143.67 & 2922.54 \\ 4978.15 & 3857.70 & 2924.02 & 3857.67 \end{pmatrix} psi$$

$$z := \begin{pmatrix} 0.996484492 & 0.998123745 & 0.999550484 & 0.998115132 \\ 0.995185262 & 0.996721757 & 0.998099069 & 0.996705843 \\ 0.991107488 & 0.993978245 & 0.996696364 & 0.99396254 \\ 0.983765673 & 0.988750123 & 0.993951744 & 0.988736657 \\ 0.974097278 & 0.980310451 & 0.988726311 & 0.980293086 \\ 0.971031739 & 0.972415586 & 0.980281452 & 0.972410385 \\ 0.984396773 & 0.971806908 & 0.972405448 & 0.971809008 \\ 1.007951149 & 0.98268934 & 0.971804698 & 0.982699827 \\ 1.057679644 & 1.009651472 & 0.982730899 & 1.009650125 \end{pmatrix}$$

below.

At block 403 an initial free volume of the sample is calculated based on the pressure and compressibility factor matrices as follows. The gauge pressures in the pressure matrix may be converted to absolute pressures for purposes of the calculations. Then, each matrix is divided into vectors for performing calculations for each pressure step run as follows:

$$Pref_i := Press^{\langle 0 \rangle} \quad Pref_f := Press^{\langle 1 \rangle} \quad Psam_i :=$$
$$Press^{\langle 2 \rangle} \quad Psam_f := Press^{\langle 0 \rangle} \quad (1)$$

$$zref_i := z^{\langle 0 \rangle} \quad zref_f := z^{\langle 1 \rangle} \quad zsam_i := z^{\langle 2 \rangle} \quad zsam_f := z^{\langle 3 \rangle} \quad (2)$$

where $Pref_i$ refers to the initial pressure of the reference cell 302, $Pref_f$ refers to the final pressure of the reference cell 302,
$Psam_i$ refers to the initial pressure of the sample cell 304,
$Psam_f$ refers to the final pressure of the sample cell 304,
$zref_i$ refers to the initial compressibility factor of the fluid in the reference cell 302,
$zref_f$ refers to the final compressibility factor of the fluid in the reference cell 302,
$zsam_i$ refers to the initial compressibility factor of the fluid in the sample cell 304, and
$zsam_f$ refers to the final compressibility factor of the fluid in the sample cell 304.

The free volume ($V_{free}$) of the sample can be calculated in block 403 from the following equation:

$$V_{free} := \frac{\left( \frac{Pref_f \cdot V_r}{zref_f} - \frac{Pref_i \cdot V_r}{zref_i} \right)}{\frac{Psam_i}{zsam_i} - \frac{Psam_f}{zsam_f}} \quad (3)$$

where $V_r$ refers to the volume of the reference cell, which is calculated at the beginning of the pressure testing, as noted above.

The free volume ($V_{free}$) calculated using Equation (3) for each of the nine test runs is shown in the following matrix:

$$V_{free} = \begin{pmatrix} 107.057 \\ 103.39 \\ 101.543 \\ 100.013 \\ 98.292 \\ 97.004 \\ 96.192 \\ 95.781 \\ 95.6 \end{pmatrix} \cdot cm^3$$

Figure 5:
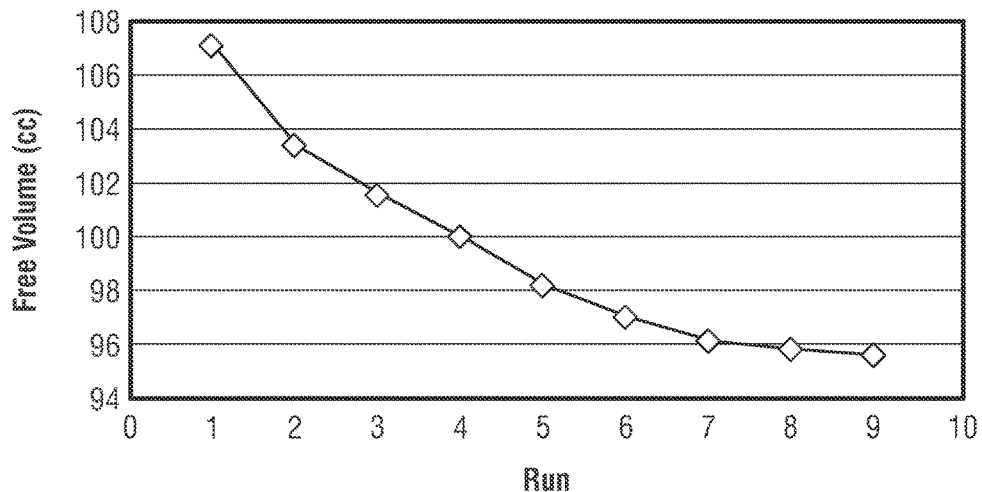
FIG. 5 illustrates the free volume calculated for an example test.

The free volume of the sample decreases as the volume of the adsorbed test gas increases. When the sample stops adsorbing, the free volume stops changing. For example, as shown in the $V_{free}$ matrix above, the free volume converges to about 96 cm$^3$ when the sample stops adsorbing. A graphical representation of the free volume as a function of pressure is shown in FIG. 5.

At block 404 the adsorption and storage capacity of the sample can be calculated based on the initial free volume ($V_{free}$) calculated in block 403. The following example describes the calculations for determining the adsorption of test gas of the sample and storage capacity of the sample based on the initially determined free volume calculated in block 403. Table 1 lists values that are used in the equations that follow for determining the adsorption of test gas of the sample.

TABLE 1

| Symbol | Definition | Value |
|---|---|---|
| T | Temperature (° C.) | 130.37 |
| Vref | Reference Volume (cc) | 91.26 |
| W | Sample Weight (grams) | 214.49 |
| Tsc | Temperature at standard conditions (° C.) | 273.15 |
| Zsc | Compressibility at standard conditions | 0.9999 |
| Psc | Pressure at standard conditions (psia) | 14.696 |
| TC | Temperature at current conditions (° K) | T + 273.15 |
| Pbar | Barometric Pressure (mm/Hg) | 762 |

Initially, a gas formation volume factor ($B_{sc}$) can be calculated as follows:

$$Bsc := \frac{Tsc \cdot Zsc}{TC \cdot Psc} = 0.049 \quad (4)$$

Then, a ratio of absolute pressure to compressibility factor ($PZ_{ratio}$) can be calculated for each pressure in the pressure matrix as follows:

$$PZ_{ratio} := \frac{Press + P_{bar}}{z} \quad (5)$$

Then, the volume adsorbed ($V_{ads0}$) for the first pressure point can be calculated in units of cubic centimeters per gram as follows:

$$V_{ads_0} := \frac{Bsc}{W} \cdot \frac{\begin{bmatrix} V_{ref} \cdot (PZratio_{ref\_i_0} - PZratio_{ref\_f_0}) + \\ V_{free} \cdot (PZratio_{sam\_i_0} - PZratio_{sam\_f_0}) \end{bmatrix}}{1 + Bsc \cdot .0017 \cdot (PZratio_{sam\_i_0} - PZratio_{sam\_f_0})} \quad (6)$$

Initially, during the testing, the sample does not contain any adsorbed gas. Thus, the gas content for the first pressure point ($GC_0$) can be expressed as:

$$GC_0 := V_{ads_0} \quad (7)$$

Then, for the additional pressure stages, the volume adsorbed for each pressure point can be added to the gas content previously calculated as follows:

$$\begin{pmatrix} V_{ads} \\ GC \end{pmatrix} := \text{for } i \in 1, 2 \ldots \text{length } (Psam_f) - 1 \quad (8)$$

$$\begin{vmatrix} V_{ads_i} \leftarrow \frac{Bsc}{W} \cdot \frac{\begin{bmatrix} V_{ref} \cdot (PZratio_{ref\_i_i} - PZratio_{ref\_f_i}) + \\ (V_{free} - GC_{i-1} \cdot W \cdot .0017) \cdot \\ (PZratio_{sam\_i_i} - PZratio_{sam\_f_i}) \end{bmatrix}}{1 + Bsc \cdot .0017 \cdot (PZratio_{sam\_i_i} - PZratio_{sam\_f_i})} \\ GC_i \leftarrow V_{ads_i} + GC_{i-1} \\ \begin{pmatrix} V_{ads} \\ GC \end{pmatrix} \end{vmatrix}$$

The gas content (GC) calculated from Equation (8) can then be converted from units of $cm^3/gm$ to units of scf/ton as follows:

$$GC(scf/ton) = GC(cm^3/gm) \times 32.037. \quad (9)$$

The matrix of values for the gas content (GC) derived from Equations (4) - (9) for the nine test runs follows:

$$GC = \begin{pmatrix} 3.942 \\ 6.621 \\ 10.75 \\ 17.09 \\ 24.882 \\ 31.303 \\ 35.165 \\ 36.648 \\ 37.448 \end{pmatrix}$$

The equilibrium pressure in absolute terms ($P_{eq}$) can be calculated as follows:

$$P_{eq} := Psam_f + P_{bar} \quad (10)$$

The matrix of the values of equilibrium pressure ($P_{eq}$) for the nine test runs is:

$$P_{eq} = \begin{pmatrix} 62.535 \\ 110.435 \\ 207.135 \\ 406.435 \\ 795.835 \\ 1.383 \times 10^3 \\ 2.159 \times 10^3 \\ 2.937 \times 10^3 \\ 3.872 \times 10^3 \end{pmatrix}$$

A ratio of respective equilibrium pressure to gas content can be calculated as follows:

$$Peq\_GC_{ratio} := \frac{P_{eq}}{GC} \quad (11)$$

The slope (a) and the intercept (b) of a best fit line (least squares) that relates the equilibrium pressure to gas content ratio as a function of pressure can be obtained by the following equation:

$$\frac{P_{eq}}{GC} = ap_{eq} + b \quad (12)$$

$$a := \text{slope } (P_{eq}, Peq\_GC_{ratio})$$

$$b := \text{intercept } (P_{eq}, Peq\_GC_{ratio})$$

Then the Langmuir coefficients can be determined from the slope and the intercept of the line derived from Equation (12) as follows:

$$V_L := \frac{1}{a} = 44.0922 \quad (13)$$

$$P_L := V_L \cdot b = 617.5556$$

The Langmuir equation can then be plotted as a function of pressure according to the following equation:

$$V(P) := V_L \cdot \frac{P}{P + P_L} \quad (14)$$

where the pressure P can be taken from the final pressure values for the sample cell 304 listed in the above pressure matrix.

Figure 6:
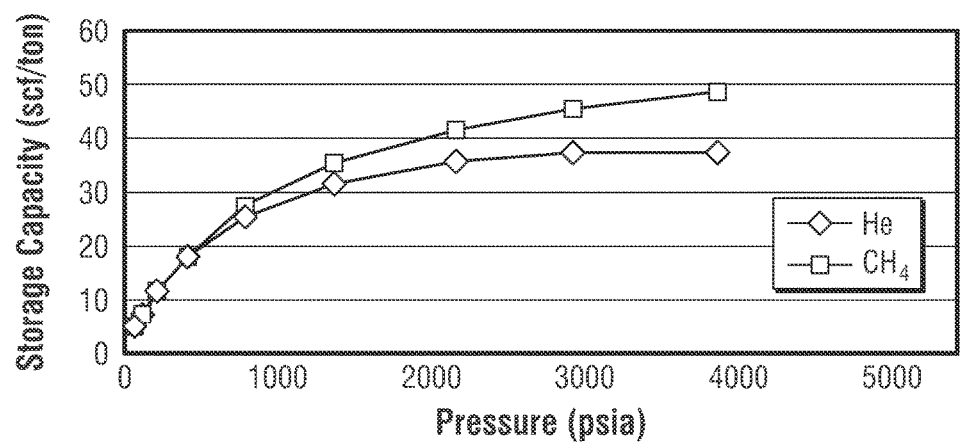
FIG. 6 shows a Langmuir curve showing gas content calculated for a first iteration of the workflow of FIG. 4.

The Langmuir curve corresponding to the example data is shown in FIG. 6. The maximum storage capacity can be identified from the Langmuir curve. As shown in FIG. 6, the maximum storage capacity occurs at a pressure of about 4000 psia (281.2 kg/square cm absolute) and is approximately 50 scf/ton (1.56 $cm^3/gm$).

As noted above, when a sample is pressurized at pressures at or above the pressure at which the storage capacity is maximized, it is assumed that the maximum amount of adsorbed gas is already present on the surface of the sample as a liquid, such that the free volume determined at or above such pressures will actually be inaccurate (i.e., will be too low).

In block 405, this inaccuracy can be corrected by calculating the maximum volume of adsorbed liquid from the maximum storage capacity derived in block 404.

Table 2 lists various values and parameters that are used to determine the maximum volume of adsorbed liquid.

TABLE 2

| Parameter | Definition | Value for Example |
|---|---|---|
| sc | Total Cumulative Storage Capacity (scf/ton) | 33.8 |
| wt | Sample Weight (grams) | 214.49 |
| $\rho_{liq}$ | Density of liquid phase at atmospheric pressure and just below boiling point (kg/m$^3$) | 422.37 |

TABLE 2-continued

| Parameter | Definition | Value for Example |
|---|---|---|
| R | Universal Gas Constant (J/K) | 8.314 |
| P | Atmospheric Pressure at standard conditions (atm) | 1 |
| T | Temperature at standard conditions (° K) | 293.15 |
| $\rho_{molar}$ | Molar Density (gm/mol) | 16.043 |
| z | Compressibility at standard conditions | 0.99814 |

The gas volume adsorbed at standard conditions ($V_{st}$) can be expressed as a function of the maximum storage capacity derived in block 404 (sc) as follows:

$$V_{st} = sc \times wt \quad (14)$$

The number of moles adsorbed (n) can be expressed as follows:

$$n = PV_{st}/RTz \quad (15)$$

The mass adsorbed ($m_{ads}$) can be calculated as follows:

$$m_{ads} = n\rho_{molar} \quad (16)$$

The maximum volume of adsorbed liquid (V) can then be calculated as follows:

$$V = m_{ads}/\rho_{liq} \quad (17)$$

Thus, from FIG. 6, for a total cumulative storage capacity of 50 scf/ton (1.56 cm³/gm), the maximum volume of adsorbed liquid is 0.5 cm³.

In block 406, the maximum volume of adsorbed liquid calculated in block 405 (in this example, 0.5 cm³) is added back to the free volume of the sample calculated in block 403 (in this example, 96 cm³) to yield an updated free volume (in this example, 96.5 cm³).

Figure 7:
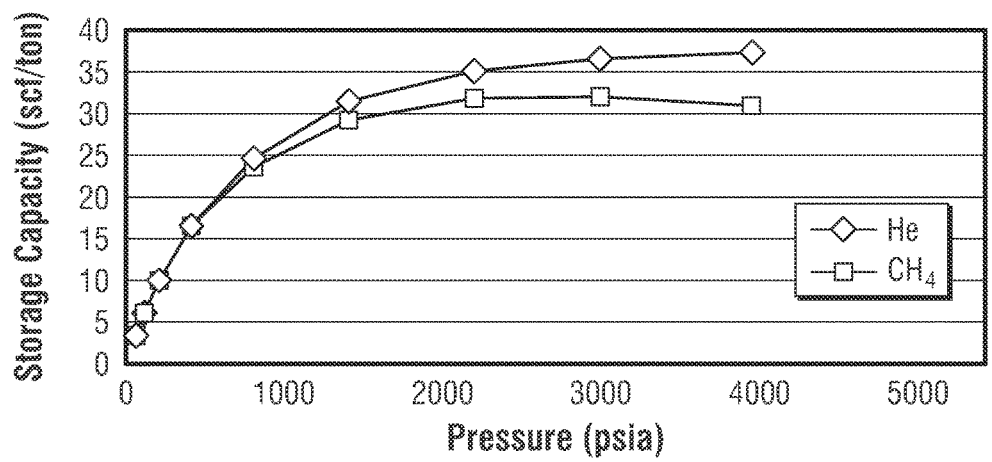
FIG. 7 shows a Langmuir curve showing gas content calculated for a second iteration of the workflow of FIG. 4.

Then, at block 407 the Langmuir curve of Equation (14) can be recalculated based on the updated value of the free volume calculated in block 406 and the pressure data from the test runs. An example of such a recalculated Langmuir curve is shown in FIG. 7. The maximum storage capacity can be identified from the Langmuir curve. As shown in FIG. 7, the maximum storage capacity occurs at a pressure of about 4000 psia (281.2 kg/square cm absolute) and is about 31 scf/ton (0.97 cm³/gm).

At block 408 the maximum storage capacity derived in block 407 can be compared to the initially determined maximum storage capacity derived in block 404. If the maximum storage capacity derived in block 407 deviates from the initially determined maximum storage capacity derived in block 404 by more than a certain amount, it may be determined that the storage capacity has not been finally determined. In this case, the operation can continue to block 410 where the liquid volume of adsorbed methane can be calculated from the maximum storage capacity derived in block 407 (e.g., using Equations (14)-(17) as described above) and then the operation continues to repeat blocks 406 to 408 to compare the maximum storage capacity derived in block 407 to the maximum storage capacity derived in the previous iteration of block 407. These iterations continue until the value of the storage capacity converges (e.g., the value does not change more than a predetermined percentage between iterations). As the value of the storage capacity converges, the value of the free volume also converges. In this case, the free volume for this fully converged storage capacity can be equated to the free volume of the sample. At this point, the process can end as shown.

Figure 8:
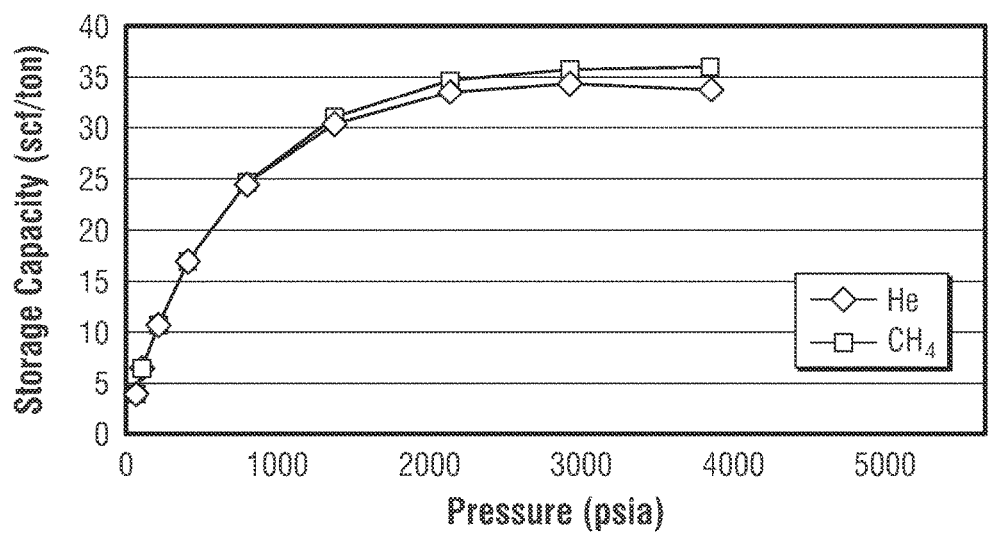
FIG. 8 shows a Langmuir curve showing gas content calculated for a final iteration of the workflow of FIG. 4.

As shown in FIG. 8, the maximum storage capacity converges to about 36 scf/ton, which is equated to the storage capacity of the sample. The free volume for this converged maximum storage capacity can then be equated to the free volume of the sample.

There have been described and illustrated herein several embodiments of a method of determining storage capacity and free volume. While particular embodiments have been described, it is not intended that the invention be limited thereto, as it is intended that the invention be as broad in scope as the art will allow and that the specification be read likewise. Thus, while a particular ordering of operations has been disclosed, it will be appreciated that other orderings may be performed as well. Moreover, while particular test apparatus configurations have been disclosed in reference to a workflow, it will be appreciated that other configurations could be used as well. It will therefore be appreciated by those skilled in the art that yet other modifications could be made to the disclosed embodiments without deviating from its scope as claimed.

What is claimed is:

1. A method of characterizing free volume of a rock sample to estimate productivity of a reservoir including:
   iteratively measuring pressure decay data during each of a plurality of pressurization stages of the rock sample pressurized with a test gas from a pressurizing source, wherein the pressure decay data comprises a beginning pressure and a final pressure subjected to by the rock sample and a beginning source pressure of the pressurizing source, and wherein the beginning source pressure is varied across the plurality of pressurizing stages such that the test gas is successively adsorbed in a pore space of the rock sample through the plurality of pressurization stages, wherein the rock sample is obtained from the reservoir and comprises a shale;
   calculating a beginning free volume available to the test gas in the rock sample based at least on the pressure decay data of a pressurization stage of the plurality of pressurization stages, wherein the beginning free volume corresponds to a pore space volume available to the test gas at a beginning of the pressurization stage;
   calculating a liquid volume of the test gas adsorbed as a liquid by the rock sample, during the pressurization stage, based at least on the pressure decay data;
   calculating an updated free volume available to the test gas in the rock sample based at least on the beginning free volume reduced by the liquid volume of the test gas adsorbed as the liquid during the pressurization stage;
   deriving an updated maximum storage capacity of storing the test gas in the rock sample based at least on the updated free volume;
   comparing the beginning free volume and the updated free volume to generate a difference;
   continuing the plurality of pressurization stages until the difference does not exceed a pre-determined threshold; and
   estimating, subsequent to reaching the difference not exceeding the pre-determined percentage, the productivity based on the updated maximum storage capacity of storing the test gas.

2. The method according to claim 1, wherein the test gas does not include helium.

3. The method according to claim 2, wherein the test gas is methane.

4. The method according to claim 1, wherein the rock sample is pressurized above a pressure corresponding to a percentage of a Langmuir volume based on a Langmuir isotherm curve.

5. The method according to claim 1, wherein the rock sample is a shale.

6. The method according to claim 5, wherein the shale has a total organic carbon content of less than 2.5%.

7. A method of characterizing free volume of a rock sample to estimate productivity of a reservoir including:
   iteratively measuring pressure decay data during each of a plurality of pressurization stages of the rock sample pressurized with a test gas from a pressurizing source, wherein the pressure decay data comprises a beginning pressure and a final pressure subjected to by the rock sample, and a beginning source pressure of the pressurizing source, wherein the rock sample comprises shale of the reservoir, wherein the test gas is successively adsorbed in a pore space of the rock sample through the plurality of pressurization stages, wherein the rock sample is obtained from the reservoir;
   calculating a beginning free volume available to the test gas in the rock sample based at least on the pressure decay data of a pressurization stage of the plurality of pressurization stages, wherein the beginning free volume corresponds to a pore space volume available to the test gas at a beginning of the pressurization stage;
   calculating a liquid volume of the test gas adsorbed as a liquid by the rock sample, during the pressurization stage, based at least on the pressure decay data;
   calculating an updated free volume available to the test gas in the rock sample based at least on the beginning free volume reduced by the liquid volume of the test gas adsorbed as the liquid during the pressurization stage;
   comparing the beginning free volume and the updated free volume to generate a difference;
   continuing the plurality of pressurization stages until the difference does not exceed a pre-determined threshold; and
   estimating, subsequent to reaching the difference not exceeding the pre-determined percentage, the productivity based on the updated free volume available to the test gas in the rock sample.

8. The method according to claim 7, wherein the test gas does not include helium.

9. The method according to claim 8, wherein the test gas is methane.

10. The method according to claim 7, wherein the rock sample is pressurized above a pressure corresponding to a percentage of a Langmuir volume based on a Langmuir isotherm curve.

11. The method according to claim 7, wherein the shale has a total organic carbon content of less than 2.5%.

* * * * *